(12) United States Patent
Reiderman et al.

(10) Patent No.: US 7,726,193 B2
(45) Date of Patent: Jun. 1, 2010

(54) ELECTROMAGNETIC ACOUSTIC TRANSDUCER WITH CROSS-TALK ELIMINATION

(75) Inventors: Arcady Reiderman, Houston, TX (US);
Stanislav W. Forgang, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 224 days.

(21) Appl. No.: 11/862,965

(22) Filed: Sep. 27, 2007

(65) Prior Publication Data
US 2009/0084185 A1   Apr. 2, 2009

(51) Int. Cl.
*G01N 29/06* (2006.01)
*G01N 29/24* (2006.01)

(52) U.S. Cl. .................. 73/643; 73/620; 367/156; 367/168

(58) Field of Classification Search .............. 73/643, 73/620, 629; 367/156, 168
See application file for complete search history.

(56) References Cited

U.S. PATENT DOCUMENTS

| | | | | |
|---|---|---|---|---|
| 3,919,498 | A * | 11/1975 | Beer | 381/408 |
| 4,296,486 | A * | 10/1981 | Vasile | 367/140 |
| 5,216,723 | A * | 6/1993 | Froeschle et al. | 381/418 |
| 5,436,873 | A * | 7/1995 | MacLauchlan et al. | 367/140 |
| 5,689,070 | A * | 11/1997 | Clark et al. | 73/643 |
| 5,763,786 | A * | 6/1998 | Camplin et al. | 73/643 |
| 5,831,596 | A * | 11/1998 | Marshall et al. | 345/161 |
| 6,070,467 | A * | 6/2000 | Rosenberg et al. | 73/643 |
| 6,192,760 | B1 * | 2/2001 | MacLauchlan et al. | 73/643 |
| 6,839,640 | B2 * | 1/2005 | Ohtani | 702/35 |
| 6,951,133 | B2 | 10/2005 | Passarelli, Jr. | |
| 7,024,935 | B2 | 4/2006 | Paige et al. | |
| 7,165,453 | B2 * | 1/2007 | Flora et al. | 73/643 |
| 2007/0131417 | A1 * | 6/2007 | Bolshakov et al. | 166/250.13 |

OTHER PUBLICATIONS

Maxwell Equation, Physics Department, UVA May 9, 2009.*
Reidierman, A.; Electromagnetic Acoustic Transducer With Cross-Talk Elimination, Jul. 26, 2007.
Nondestructive Testing Encyclopedia-Magnetic Particle Inspection, www.ndt.net, Mar. 26, 2007.

* cited by examiner

*Primary Examiner*—J M Saint Surin
(74) *Attorney, Agent, or Firm*—Bracewell & Giuliani LLP

(57) ABSTRACT

The electromagnetic acoustic transducer (EMAT) transducer disclosed herein is useful for the non-destructive analysis of objects. The transducer comprises a core having a winding and a coil disposed between the core and the object to be analyzed. One transducer can be used as a transmitter and another transducer as a receiver. Then selectively switching static magnetic field in either transmitter or receiver and processing data with and without static magnetic field allows for eliminating artifacts due to parasitic coupling between the transmitter/receiver pair. The switching of the static magnetic field can be implemented either by using electromagnet or a pair of permanent magnets where magnetization of one permanent magnet is reversed to provide cancellation of the static magnetic field.

15 Claims, 4 Drawing Sheets

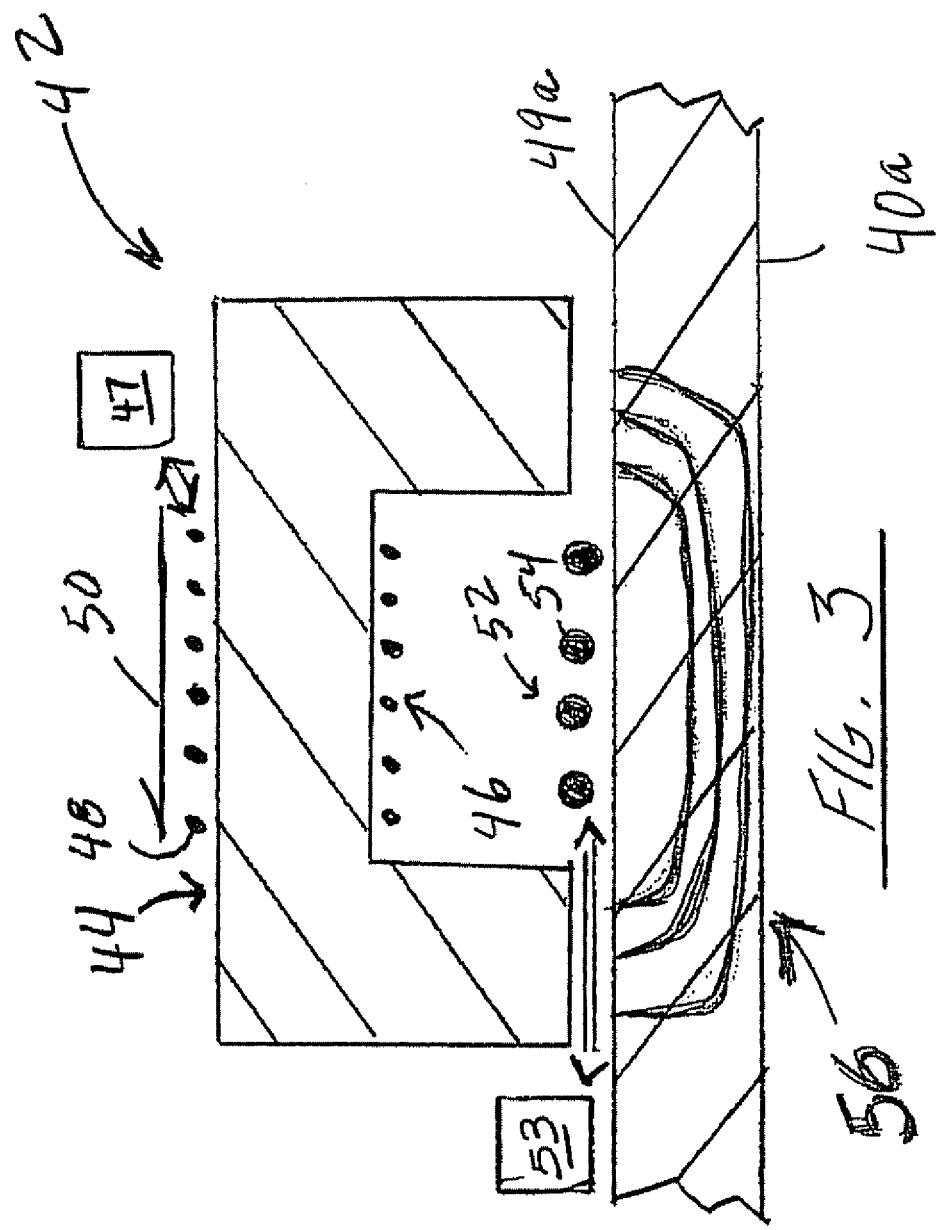

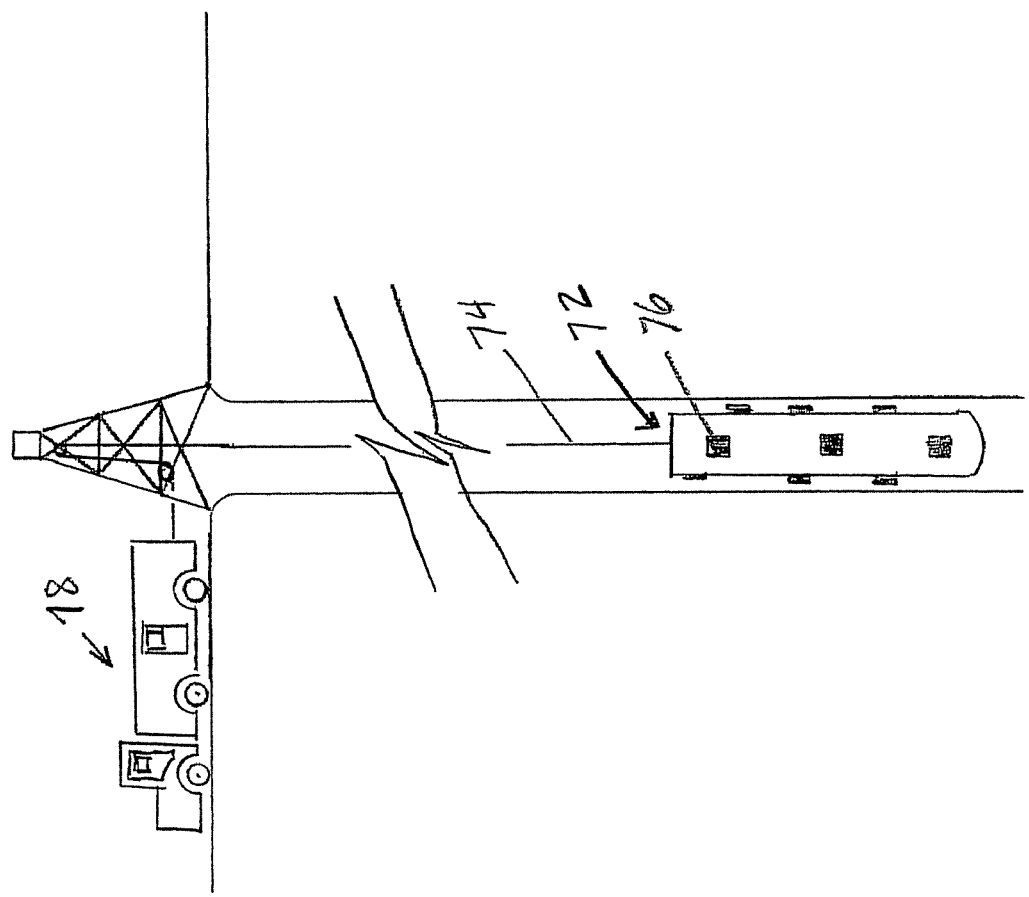

ELECTROMAGNETIC ACOUSTIC TRANSDUCER WITH CROSS-TALK ELIMINATION

BACKGROUND OF THE INVENTION

1. Field of the Invention

The disclosure herein relates generally to the field of electromagnetic transducers. More specifically, the present disclosure relates to an electromagnetic acoustic transducer used in non-destructive testing. Yet more specifically, described herein is a method and apparatus for eliminating interference between separate electromagnetic acoustic transducers.

2. Description of Related Art

Monitoring the behavior of acoustic waves in a solid is useful in detecting potential flaws in the solid. One example of use includes propagating an acoustic wave into a member being testing, receiving the resulting wave, and analyzing the wave. Determining the resulting wave's attenuation can yield useful information concerning flaws in the member. The flaws may include cracks, pitting, corrosion, or other discontinuities in the solid. The members being tested include structural members, vessels, piping and other tubulars. Other applications include measuring solid dimensions and identifying the material through which the wave propagates.

One device useful for inducing acoustic waves in solids for non-destructive testing is an electromagnetic acoustic transducer (EMAT). FIG. 1 illustrates in a side cut-away view an example of a prior art EMAT 10. The EMAT 10 comprises a permanent magnet 14 that extends substantially parallel to an electrically conductive object 12. Members disposed on the terminal ends of the magnet 14 form a magnetic yoke 16 extending downward toward the object 12. A coil 18 comprising a series of wires 20 is disposed in the space between the permanent magnet 14 and the object 12.

EMAT function comprises flowing electrical current through the coil 18 thereby inducing eddy currents in the object 12 proximate to the electrically conducting wire 20. Interaction between a magnetic field and induced eddy currents in turn creates Lorentz forces that acoustically excite the object. The magnetic field is produced by the magnet 14. Acoustic excitation typically results in acoustic waves that propagate in the object 12. Similarly, placing an EMAT proximate to an object excited by acoustic waves can induce an alternating magnetic flux that in turn results in an electromotive force applied to the receiver coil wires. Thus by measuring this electromotive force an EMAT may also act as an acoustic receiver. Recording and analyzing these waves is useful in detecting flaws in the solid.

One drawback of currently used EMATs is if an EMAT transmitter and an EMAT receiver are sufficiently proximate on another, parasitic coupling, or cross-talk, occurs between the respective windings of the transmitter and receiver. The resulting cross talk can have deleterious effects on data received by the receiver.

BRIEF SUMMARY OF THE INVENTION

Disclosed herein is an electromagnetic acoustic transducer useful for analyzing an object comprising, a magnetic core, a core winding circumscribing the core, wherein the winding is configured for flowing current therethrough, and a coil configured for conducting an alternating current. The transducer may optionally further comprise a permanent magnet, wherein selectively flowing current through the winding can change polarity of magnetization of the magnetic core thereby selectively canceling the resulting magnetic field of the core and magnet. The core preferably comprises a permanent magnet or a soft magnetic material.

A method of analyzing a solid is disclosed comprising disposing first and second electromagnetic acoustic transducer proximate to the solid, wherein the first electromagnetic acoustic is a transmitter and the second electromagnetic acoustic transducer is a receiver; selectively switching off a static magnetic field in one of the electromagnetic acoustic transducers; generating an acoustic signal with the first electromagnetic acoustic transducer; and receiving acoustic data with and without the presence of said static magnetic field in order to eliminate the data artifacts due to parasitic coupling between the transmitting electromagnetic acoustic transducer and the receiving electromagnetic acoustic transducer.

BRIEF DESCRIPTION OF THE SEVERAL VIEWS OF THE DRAWING

FIG. 3 is a cut-away side view of an alternative embodiment of an electromagnetic acoustic transducer.

FIG. 4 is an embodiment of a downhole tool having an electromagnetic acoustic transducer.

DETAILED DESCRIPTION OF THE INVENTION

The present disclosure concerns an electromagnetic transducer with the capability of eliminating cross-talk that sometimes occurs between a transmitting transducer and a receiving transducer. Cross-talk is also referred to herein as a parasitic signal due to direct coupling between the transmit and receive coils of a respective transmitter and receiver. One manner of eliminating artifacts due to the cross-talk involves neutralizing or removing the magnetic field induced by a transducer in the object being analyzed. The signal recording without the magnetic field (either on transmitter or receiver side) represents the cross-talk related signal only. Subtracting this signal from the signal recording in full magnetic field mode gives acoustic propagation signal without artifacts due transmitter-receiver electromagnetic cross-talk. For the purposes of discussion herein, the term "artifact": refers to an unwanted signal or a portion of a signal that is unwanted. One example of an artifact is noise or coherent noise. As discussed below, the magnetic field can be removed either by removing current in the electromagnet, or by creating a "canceling" permanent magnetic field. A canceling magnetic field refers to one created proximate to interact with a first magnetic field, where the canceling magnetic field has a magnitude and polarity that substantially negates the first magnetic field.

Figure 1:
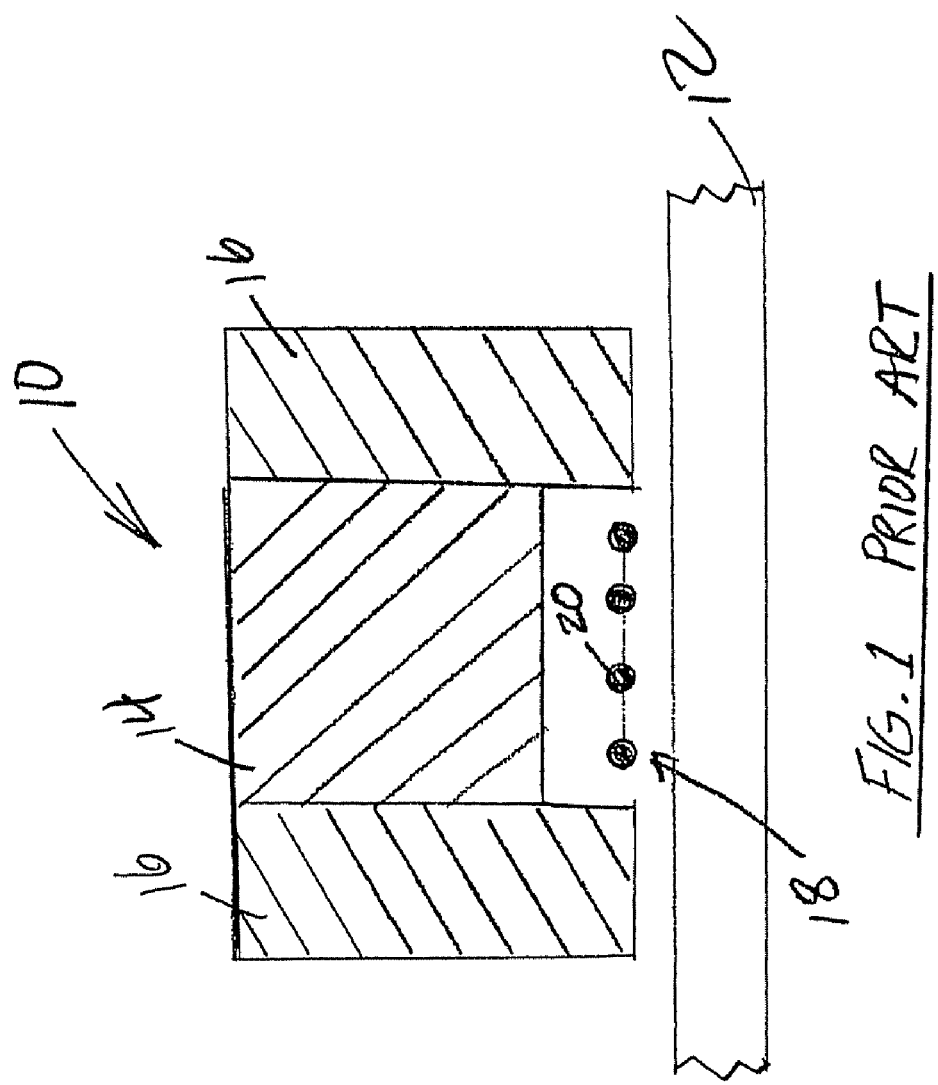
FIG. 1. is a cut-away side view of a prior art electromagnetic acoustic transducer.
Figure 2A:
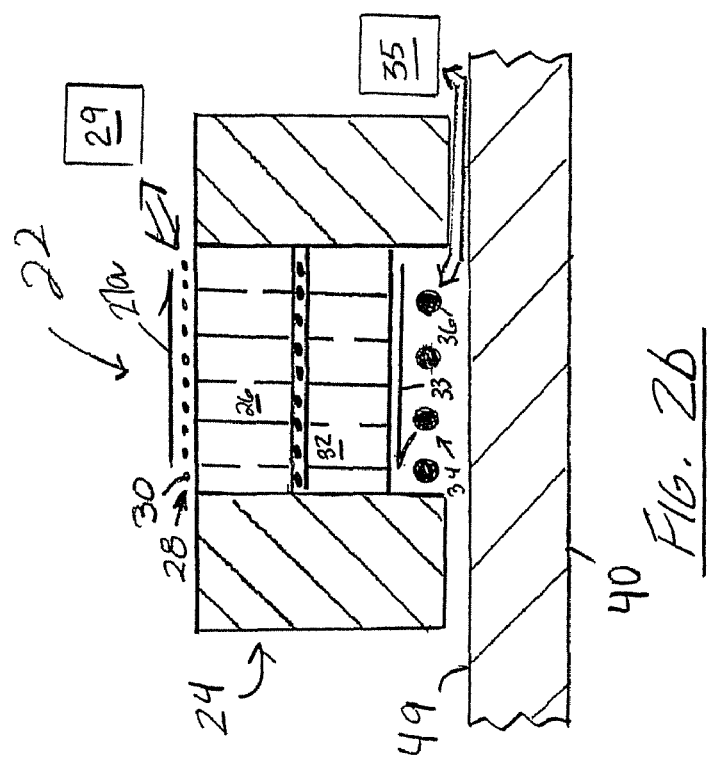
FIGS. 2a and 2b are cut-away side views of operational modes of an embodiment of an electromagnetic acoustic transducer.
Figure 2B:
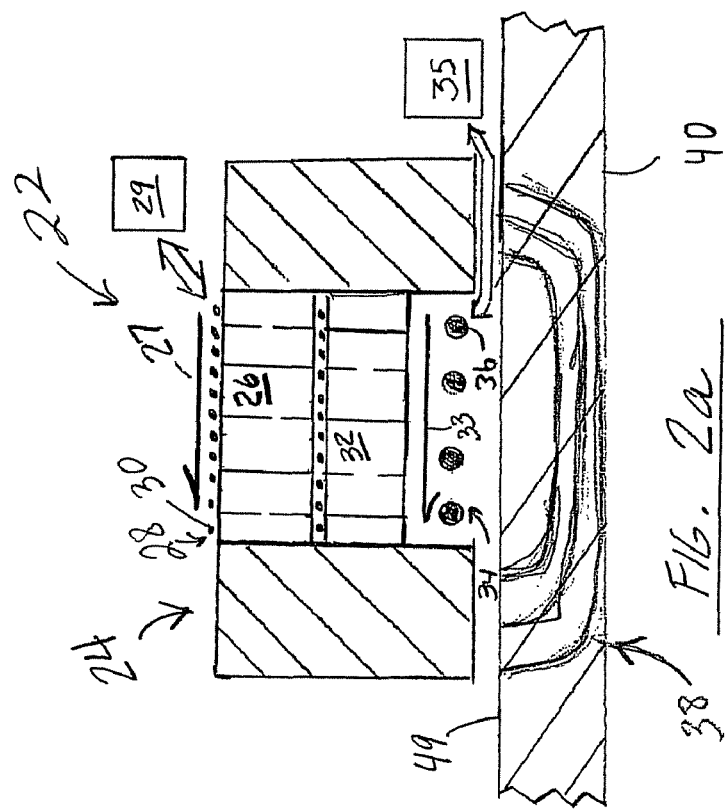

With reference to FIGS. 2a and 2b one embodiment of an electromagnetic transducer in accordance with the present disclosure is provided in a side cutaway view. In FIG. 2a a transducer 22 is shown comprising a core 26 bound by a winding 28. In this embodiment the core 26 comprises a magnetic material with substantial magnetic hysteresis. In the embodiment shown, the winding 28 comprises an elongated length of wire 30 coaxially wrapped along a portion of the core 26. A magnetic yoke 24, comprising a soft magnetic material, is coupled with the terminal ends of the core 26. The magnetic yoke 24 extends downward towards the surface of the object 40 that is being examined by the transducer 22. The yoke 24 conducts magnetic flux from the core end poles to the object being tested.

Disposed substantially parallel to and below the core 26 is a permanent magnet 32, in the embodiment shown the magnet 32 operates as a magnetic field source that generates a magnetic field. The permanent magnet 32 is also bound on its terminal ends by the magnetic yoke 24.

As shown via the double-headed arrow, the windings 28 are in electrical communication with a pulsed current source 29. The current source 29 selectively provides electrical pulsed power to the windings 28. The pulsed power is sufficient to magnetize/re-magnetize the magnetic core 26. Due to magnetic hysteresis the magnetic core 26 remains magnetized after the pulsed current produced by the current source 29 ends. The magnetization directions of the core 26 and the permanent magnet 32 are shown by arrows 27 and 33 respectively in FIG. 2a. In the acoustic wave generation mode of the transducer 22 presented in FIG. 2a, the residual magnetization of the core 26 and magnetization of the permanent magnet 32 are in the same direction. The resulting magnetic field produced by the magnetized core 26 and the permanent magnet 32 is illustrated by the series of flux lines 38 extending through the object.

A coupling winding 34 is shown in the embodiment of FIG. 2a in the space provided between the permanent magnet 32 the object upper surface 49. In this embodiment the coupling winding 34 comprises a coupling winding wire 36, wherein the wire 36 is elongated and electrically conducting. This wire 36 is shown formed in a standard series of loops, in one embodiment the wire 36 may comprise a meander wire. A current source 35 of RF current is shown in electrical communication with the coupling winding 34 via the double-headed arrow. Thus, by driving RF current through the coupling winding 34 in the presence of the magnetic field 38, the resulting forces on the object 40 thereby create acoustic waves within the object 40. In a receive mode of the transducer 22 operation the coupling winding 34 is connected to a receiver (not shown in FIG. 2).

FIG. 2b, shown in side cross-sectional view similar to FIG. 2a, represents an alternative mode of operation of the transducer 22. In this mode the pulsed current source 29 selectively provides pulsed current to the coil 28 in a direction that reverses the core magnetization polarity opposite from that of the mode of FIG. 2a. Due to substantial magnetic hysteresis of the magnetic material of the core 26, the core remains magnetized after the pulse of current. The opposite polarity is shown by the direction of the arrow 27a, which points in the direction opposite that of arrow 27. This reverse in polarity causes the core 26/winding 28 combination to produce a magnetic field having a polarity opposite of the magnetic field produced by the permanent magnet 32. Interacting two oppositely polarized magnetic fields (or introducing a canceling magnetic field to another magnetic field) cancels both fields.

As such, there is no resulting magnetic field extending into the body of the object 40. The signal recording taken while generating the compensated magnetic field is subtracted from the signal recording taken with the full magnetic field to obtain a clean signal. The cross-talk elimination as described above can be achieved by canceling the static magnetic field of one of the receiving or transmitting transducer.

FIG. 3 provides an alternate embodiment shown in a side cross-sectional view. In this embodiment the transducer 42 comprises a core 44 that has a substantially U-shaped cross section. As shown, a winding 46 is wrapped around the longitudinal portion of the core 44. The double-headed arrow represents electrical communication between the electrical current source 47 and the winding 46. A coupling coil 52 disposed between the core 44 and the object 40a is shown in cross-sectional view and comprises an electrically conductive elongated wire 54 arranged in a typical winding pattern. With respect to the present disclosure, the winding pattern of the wire 54 can be any pattern useful for the coupling of the transducer with the object 40a for creating the requisite acoustic waves. Electrically coupled with the coil 52 is a current source 53, the coupling is shown by virtue of the double-headed arrow. As with the transducers of FIG. 2a energizing the coil 46 with the electrical current source 47 results in a resulting magnetic field that extends into the body of the object 40a. This magnetic field in the object 40a is illustrated by the series of curved lines 56. This magnetic field in combination with eddy currents induced in the object 40a as a response to the magnetic field of the energizing the coil 52 in turn produces the acoustic waves within the body of the object 40a.

In this embodiment the current source 47 is selectable to turn the supplied current to an on and off manner thereby eliminating the magnetic field 56. By synchronizing elimination of the magnetic field, along with the acquisition phase, the artifacts due to the cross-talk between an acoustic transmitter and an acoustic receiver can be eliminated.

With reference now to FIG. 4 one embodiment of a wellbore interrogation system in accordance with the present disclosure is shown in a side view. In this embodiment a downhole tool 72 is shown disposed within a wellbore via wireline 74. Transducers 76 are provided on the surface of the downhole tool 72. In this embodiment the transducers 76 may comprise an EMAT configuration and may be a combination of transmitters as well as receivers. Additionally, when disposed in a cased hole, the downhole tool 72 is useful for determining information regarding the casing and the casing bonding. Optionally, the transducers 76 can be used to obtain information regarding the formation surrounding the wellbore.

In this embodiment a surface truck 78, disposed at the surface, is used for controlling and operating the insertion and retrieval of the downhole tool 72. Optionally an information handling system (IHS) may be used in conjunction with the surface truck 78 for acquisition, recordation, as well as analysis of any acoustical or other retrieved signal data obtained by use of the transducer 76.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. The current source used for provided electrical power to the embodiments discussed may be disposed with the device, such as within a wellbore, or away from the device and coupled with a conductive member, such as a wire. This and other similar modifications will readily suggest themselves to those skilled in the art, and are intended to be encompassed within the spirit of the present invention disclosed herein and the scope of the appended claims.

What is claimed is:

1. An electromagnetic acoustic transducer useful for analyzing an object comprising:
   a core;
   an electrically conductive core winding circumscribing the core in selective communication with a current source;
   a magnetic field source, so that when the transducer is disposed proximate the object and pulsed current flows from the current source through the core winding in one direction the core is magnetized and with the magnetic field source produces a magnetic field that combined with a magnetic field from the magnetic field source to produce a resultant magnetic field in the object and when the current flows through the winding in an opposite direction a magnetic field is produced that cancels the magnetic field from the magnetic field source;

an electrically conductive coil in electrical communication with a current supply of RF current, so that when the current supply supplies current acoustic waves are produced in the object.

2. The transducer of claim 1, wherein the magnetic field source comprises a permanent magnet.

3. The transducer of claim 1, wherein the current flowing through the core winding has a selectable direction.

4. The transducer of claim 1, wherein the core comprises a permanent magnet having a changeable polarity.

5. The transducer of claim 2 further comprising a magnetic yoke disposed on the terminal end of the core and the magnetic field source.

6. The transducer of claim 1 further comprising a current source in communication with the core winding.

7. The transducer of claim 1 further comprising an alternating current source in communication with the coil.

8. The transducer of claim 1, wherein the transducer operates as an acoustic transmitter.

9. The transducer of claim 1, wherein the transducer operates as an acoustic receiver.

10. The transducer of claim 1 further comprising a downhole tool disposable within a tubular.

11. A method of analyzing a solid comprising:
(a) creating a magnetic field in the object;
(b) generating an acoustic signal in the object by driving RF current through a coupling winding in the presence of the magnetic field;
(c) selectively cancelling the magnetic field; and
(d) monitoring the acoustic signal in the object.

12. The method of claim 11, further comprising providing an electromagnetic acoustic transducer comprising: a core, an electrically conductive core winding circumscribing the core and in selective communication with a current source, a magnetic field source, a coupling winding in communication with a RF current supply; wherein step (a) is performed by flowing current through the core winding in a first direction and wherein step (b) is performed by flowing RF current through the coupling winding.

13. The method of claim 12 further comprising disposing the transducer within a wellbore.

14. The method of claim 12, wherein step (c) of claim 11 is performed by flowing current through the core winding in an opposite direction.

15. The method of claim 14, further comprising subtracting the acoustic signal recorded during step (b) from the signal recorded during step (c) to obtain a clean signal.

* * * * *